(12) United States Patent
Biber et al.

(10) Patent No.: US 11,307,273 B2
(45) Date of Patent: Apr. 19, 2022

(54) LINE WITH SENSOR FOR DETECTING LINE-CONDUCTED INTERFERENCE IN A MAGNETIC RESONANCE TOMOGRAPHY APPARATUS

(71) Applicant: Siemens Healthcare GmbH, Erlangen (DE)

(72) Inventors: Stephan Biber, Erlangen (DE); Markus Vester, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/039,278

(22) Filed: Sep. 30, 2020

(65) Prior Publication Data

US 2021/0103018 A1 Apr. 8, 2021

(30) Foreign Application Priority Data

Oct. 2, 2019 (EP) ...................... 19201066

(51) Int. Cl.
*G01R 33/34* (2006.01)
*A61B 5/055* (2006.01)
*G01R 33/36* (2006.01)
*G01R 33/54* (2006.01)

(52) U.S. Cl.
CPC ........ *G01R 33/34053* (2013.01); *A61B 5/055* (2013.01); *G01R 33/36* (2013.01); *G01R 33/543* (2013.01)

(58) Field of Classification Search
CPC .......... G01R 33/34053; G01R 33/36; G01R 33/543; G01R 33/5659; G01R 33/3685; G01R 33/422; G01R 33/48; A61B 5/055

See application file for complete search history.

(56) References Cited

U.S. PATENT DOCUMENTS

| | | |
|---|---|---|
| 8,816,684 B2 | 8/2014 | Walsh |
| 2004/0164739 A1 | 8/2004 | Peterson |
| 2008/0048658 A1 | 2/2008 | Hushek |
| 2008/0315879 A1 | 12/2008 | Saha |
| 2014/0155732 A1 | 6/2014 | Patz |

(Continued)

FOREIGN PATENT DOCUMENTS

| | | |
|---|---|---|
| EP | 3467531 A1 | 4/2019 |
| JP | H04109933 A | 4/1992 |

(Continued)

OTHER PUBLICATIONS

Bulumulla, S. B., et al. "Inductively coupled wireless RF coil arrays." Magnetic resonance imaging 33.3 (2015) 351-357.

(Continued)

*Primary Examiner* — Susan S Lee
(74) *Attorney, Agent, or Firm* — Lempia Summerfield Katz LLC

(57) ABSTRACT

A line for an electrical connection in a magnetic resonance tomography apparatus and a magnetic resonance tomography apparatus with a corresponding line are provided. The line includes an electrical interference conductor that may pick up an electromagnetic interference signal from an environment and/or irradiate the electromagnetic interference signal into the environment. The line also includes a sensor that is electrically and/or magnetically coupled to the interference line.

17 Claims, 4 Drawing Sheets

(56) References Cited

U.S. PATENT DOCUMENTS

| | | | |
|---|---|---|---|
| 2014/0253119 A1* | 9/2014 | Walsh | G01V 3/38 324/309 |
| 2017/0108569 A1 | 4/2017 | Harvey | |
| 2018/0292480 A1 | 10/2018 | Brunner | |
| 2019/0025389 A1 | 1/2019 | Mcnulty | |
| 2020/0249292 A1 | 8/2020 | Biber | |

FOREIGN PATENT DOCUMENTS

| | | |
|---|---|---|
| WO | 2013016639 A1 | 1/2013 |
| WO | 2019068687 A2 | 4/2019 |

OTHER PUBLICATIONS

European Search Report for European Application 19201066.8-010 dated Mar. 24, 2020.

* cited by examiner

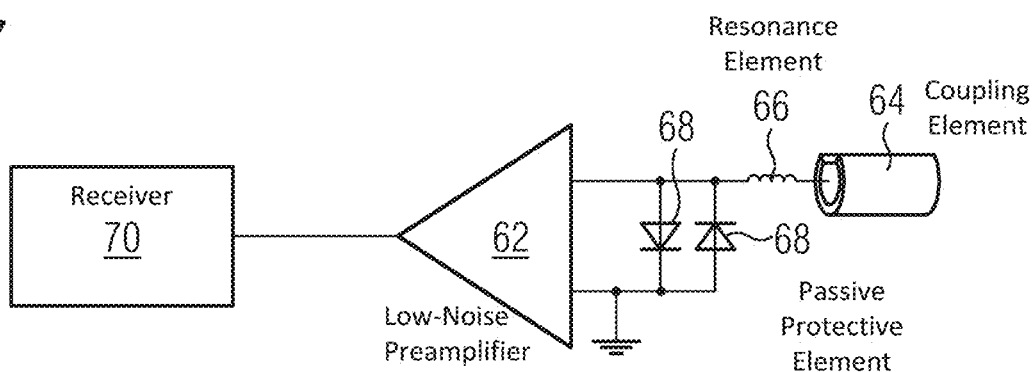

LINE WITH SENSOR FOR DETECTING LINE-CONDUCTED INTERFERENCE IN A MAGNETIC RESONANCE TOMOGRAPHY APPARATUS

This application claims the benefit of European Patent Application No. EP 19201066.8, filed on Oct. 2, 2019, which is hereby incorporated by reference in its entirety.

BACKGROUND

The present embodiments relate to a line for an electrical connection in a magnetic resonance tomography apparatus with a connector to the magnetic resonance tomography apparatus.

Magnetic resonance tomography apparatuses are imaging apparatuses that, in order to image an examination object, align nuclear spins of the examination object with a strong external magnetic field and excite the nuclear spins by an alternating magnetic field to precession about this alignment. The precession or return of the spins from this excited state into a lower energy state generates a response in the form of an alternating magnetic field that is received by antennas.

Magnetic gradient fields are used to impart spatial encoding to the signal that subsequently enables the assignment of the received signal to a volume element. The received signal is then evaluated, and a three-dimensional imaging depiction of the examination object is provided. The signal may be received using local receive antennas (e.g., local coils) that, to achieve a better signal-noise ratio, are arranged directly on the examination object. The receive antennas may also be installed in a patient bench.

Magnetic resonance tomography apparatuses require radio-frequency screening in two respects. On the one hand, radio-frequency pulses with powers in the kilowatt range are generated to excite the nuclear spins, which are only partially absorbed in the patient. Radio waves leaving the patient leadthrough are emitted into the room and are therefore to be screened to comply with emission limits.

Conversely, the magnetic resonance signals to be received for imaging are extremely weak. In order to achieve a sufficient signal-to-noise ratio (SNR), it is necessary to screen external interference signals.

As a result of this, in the prior art, complex screening cabins are installed around a magnetic resonance tomography apparatus in order to reduce both emissions and immissions.

SUMMARY AND DESCRIPTION

The scope of the present invention is defined solely by the appended claims and is not affected to any degree by the statements within this summary.

The present embodiments may obviate one or more of the drawbacks or limitations in the related art. For example, outlay for screening may be reduced.

The line according to an embodiment is provided for an electrical connection in a magnetic resonance tomography apparatus and includes electrical conductors that are able to carry an electric current. Due to the electrical conductivity, the conductors also function as antennas for electromagnetic waves and may therefore pick up or emit electrical interference capacitively or by induction and also relay the electromagnetic waves along extension of the conductors (e.g., in a screened region). The line according to the present embodiments includes a connector (e.g., a fixed electrical connection or electrical plug-in connection with the magnetic resonance tomography apparatus).

The line includes an electrical interference conductor. In this context, this may be a conductor enabled by an arrangement or interconnection of the conductor to transmit an interference signal. Herein, for the purposes of the present embodiments, an interference signal is considered to be any signal that does not contribute to the image acquisition and may impair the quality of the images provided. Therefore, herein, this may also entail signals that are necessary for image acquisition, but do not directly carry image information. Examples include interference on power supply lines, control lines, communication lines, such as, for example, facilities for communicating with the patient or lighting in the patient tunnel. However, in this context, lines that are directly relevant for image generation such as gradient coil connector lines, shim current lines, and the signals thereof may result in artifacts during image acquisition; in this context, these are considered to be interference conductors.

Herein, the electrical interference conductor may also be a conductor in the line that is actually provided to protect the signal lines in the line against interference signals. For example, an outer conductor in a coaxial line may also itself introduce interference signals as a conductor into a screened room. In one embodiment, a plurality of conductors or wires in a line may be interference conductors.

Herein, the feature that the interference conductor is configured to pick up an electromagnetic interference signal from the environment and/or irradiate the signal into the environment only indicates that this is possible due to the electrical properties and the arrangement of the interference conductor and, as a result this, represents a potential source for the introduction of interference. However, it is not necessary in the sense that the interference conductor is or will be exposed to an additional signal.

The line according to the present embodiments also includes a sensor that is electrically and/or magnetically coupled to the interference line.

The sensor is or may be connected to the magnetic resonance tomography apparatus via a signal connection via which the interference signal picked up by the interference conductor may be relayed to a control system of the magnetic resonance tomography apparatus. This enables the control system to recognize the interference signal known in this way in the magnetic resonance signals and to suppress the interference signal.

In one embodiment, the connector line according to the present embodiments with a sensor enables interference signals on lines to be identified and/or acquired (e.g., at the source or at a location where the interference signals are clearly separate from the useful signals so that the interference signals may subsequently be effectively suppressed during the image acquisition).

In one possible embodiment of the line, the sensor includes a coil or an induction loop for inductive coupling to the interference conductor. Herein, the coil, with an area enclosed by a coil winding or windings, may be substantially aligned perpendicular to magnetic field vectors generated by the interference signal currents on the interference signal conductor. Herein, substantially perpendicular may be that an angle enclosed by the normal vector of the area and the magnetic field vector is smaller than 30 degrees, 20 degrees, or 10 degrees.

An inductive coupling by a coil provides a galvanically isolated coupling to the interference conductor.

In one embodiment of the connector line, the interference conductor is arranged within an area enclosed by a coil winding or windings.

The arrangement around the line permits simple mechanical fastening and is insensitive to small changes in position.

In one embodiment of the line, the coil is a toroidal coil that encloses the interference conductor. In other words, the coil conductor is wound around a toroid on a closed path, which encloses the interference conductor and/or the line. Herein, the toroid may be a solid or hollow winding former or even only indicate a virtual geometric shape in which the coil conductor is wound. Herein, the toroid may be free of ferrites or other materials that are not suitable for the high magnetic fields or impair the magnetic resonance measurement in some other way.

The toroidal coil is particularly sensitive to magnetic fields that are generated by the current-carrying interference conductor and surround the toroidal coil in an annular shape, and simultaneously permits electrically and mechanically robust fastening.

In one embodiment of the line, the sensor includes a capacitive coupling element for coupling to the interference conductor. For example, a flat conducting element that is pressed separately onto the line by a dielectric or surrounds the line as a pipe section or as two half-shells may be provided.

In one embodiment, a capacitive coupling is particularly sensitive to interference with a high-impedance source.

In one embodiment of the line, the sensor may include a directional coupler. A directional coupler may be any coupling facility that, as a coupling element, supplies a signal that is dependent on the propagation direction of an interference signal on the interference conductor. A directional coupler may, for example, be implemented by strip transmission lines parallel to the interference conductor or transformers.

A directional coupler may distinguish whether a signal is traveling from a local coil or is moving in the direction of the local coil. Although interference going in the direction of the local coil during image acquisition is problematic, parasitic magnetic resonance signals only result in artifacts if the parasitic magnetic resonance signals are erroneously thought to be interference signals and an attempt is made to compensate the parasitic magnetic resonance signals. Herein, a directional coupler permits the separation of the two signals and the suppression of only the interference signals.

In one possible embodiment of the line, the sensor resonates at a Larmor frequency of the magnetic resonance tomography apparatus. Herein, the Larmor frequency refers to the magnetic resonance frequency of the nuclear spins to be acquired in the static magnetic field B0 of the magnetic resonance tomography apparatus. With inductive coupling using a coil, resonance may, for example, be achieved by a capacitance connected to the coil.

For imaging, with a magnetic resonance tomography apparatus, magnetic resonance signals are acquired from nuclear spins with the Larmor frequency. Therefore, the image acquisition is particularly sensitive to interference with this frequency. A sensor that resonates at this frequency may acquire the particularly relevant interference signals with a higher amplitude and hence more efficiently.

In one embodiment of the line, the sensor is protected against an excitation pulse of the magnetic resonance tomography apparatus. The excitation pulse for the nuclear spins with powers of up to a kilowatt at the Larmor frequency may (e.g., with a sensor that resonates at this frequency) result in damage to input elements. Therefore, the sensor may, for example, include passive diodes for short-circuiting the voltages that occur above the cut-off voltage. Active circuits that detune the sensor controlled by the control system are also possible.

In one embodiment, the protective elements prevent damage to the sensor caused by the magnetic resonance tomography apparatus.

In one possible embodiment of the magnetic resonance tomography apparatus, the sensor is arranged adjacent to a patient tunnel. Here, the patient tunnel indicates the location at which magnetic resonance signals are received for image acquisition and is therefore particularly sensitive to interference. Herein, adjacent is considered to be a distance that is shorter than 50%, 20%, or 10% of the length of the line or a vacuum wavelength of a radio wave at the Larmor frequency of the magnetic resonance tomography apparatus.

The arrangement of the sensor on the line in the vicinity or adjacent to the patient tunnel provides that as little interference as possible is irradiated between the sensor and patient tunnel but not acquired by the sensor.

BRIEF DESCRIPTION OF THE DRAWINGS

FIG. 7 is a schematic depiction of a sensor of an embodiment of the line.

DETAILED DESCRIPTION

Figure 1:
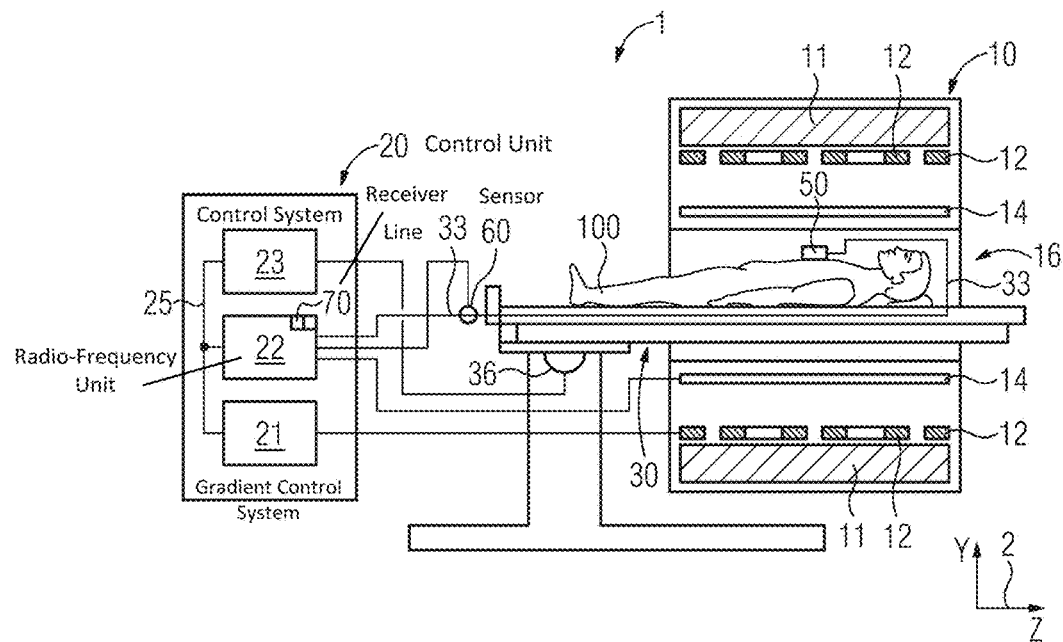
FIG. 1 is a schematic depiction of a magnetic resonance tomography apparatus with a line according to an embodiment.

FIG. 1 is a schematic depiction of an embodiment of a magnetic resonance tomography apparatus 1 with a line (e.g., a cable) 33 according to an embodiment with a sensor 60.

The magnetic unit 10 includes a field magnet 11 that generates a static magnetic field B0 for aligning nuclear spins of samples or a patient 100 in a recording region. The recording region is characterized by an extremely homogeneous static magnetic field B0, where the homogeneity relates, for example, to the magnetic field strength or the magnitude. The recording region is almost spherical and arranged in a patient tunnel 16 that extends in a longitudinal direction 2 through the magnetic unit 10. A patient bench 30 may be moved in the patient tunnel 16 by a drive unit 36. The field magnet 11 is usually a superconducting magnet that may provide magnetic fields with a magnetic flux density of up to 3T or even more with the most up-to-date devices. However, permanent magnets or electromagnets with normally conducting coils may also be used for lower field strengths.

The magnetic unit 10 also includes gradient coils 12 configured to overlay variable magnetic fields in three spatial directions on the magnetic field B0 in order to spatially differentiate the acquired imaging regions in the examination volume. The gradient coils 12 may consist of normally conducting wires that are able to generate mutually orthogonal fields in the examination volume.

The magnetic unit 10 likewise includes a body coil 14 that is configured to irradiate a radio-frequency signal supplied via a signal line into the examination volume and to receive resonance signals emitted from the patient 100 and output the resonance signals via a signal line.

A control unit 20 supplies the magnetic unit 10 with the different signals for the gradient coils 12 and the body coil 14 and evaluates the received signals.

Thus, the control unit 20 includes a gradient actuator 21 that is configured to supply the gradient coils 12 via feed lines with variable currents, which, when timing is coordinated, provide the desired gradient fields in the examination volume.

The control unit 20 also includes a radio-frequency unit 22 that is configured to generate a radio-frequency pulse with a predetermined temporal course, amplitude, and spectral power distribution in order to excite a magnetic resonance of the nuclear spins in the patient 100. Herein, pulse powers in the kilowatt range may be achieved. The excitation pulses may be irradiated into the patient 100 via the body coil 14 or also via a local transmit antenna.

A control system 23 communicates via a signal bus 25 with the gradient control system 21 and the radio-frequency unit 22.

A local coil 50 is arranged on the patient 100 and connected to the radio-frequency unit 22 and the receiver 70 thereof via a line 33. However, the body coil 14 may receive magnetic resonance signals and relay the magnetic resonance signals to the receiver 70.

The patient tunnel may have a radius R for which the following applies:

$$R < (\text{Lambda}_L * 1.841)/(2*\text{Pi})$$

Lambda$_L$ is herein the wavelength of radio wave in air at the Larmor frequency of the magnetic resonance tomography apparatus 1. If the radius R is less than the right-hand term, the radio wave is propagated with exponential attenuation in the patient tunnel 16, and the interference signal is heavily attenuated in the middle of the examination region FoV. Lambda$_L$ is also referred to as the limit wavelength of a round hollow conductor and the associated frequency as the limit frequency.

However, electromagnetic signals that are introduced into the patient tunnel 16 by an electrical conductor such as the line 33 are not subject to exponential attenuation because the line 33 interacts with a conducting wall of the patient tunnel such as a coaxial conductor. The interference may be introduced by induction or capacitively outside the patient tunnel 16 (e.g., onto a screening of the line 33). The line 33 then acts an interference conductor in the sense of the present embodiments.

Consequently, the local coil 50 receives a mixture of a magnetic resonance signal and interference signals, which are introduced into the patient tunnel 16 inter alia via interference conductors. Active interference suppression, with which the interference signal is scaled and added with a reversed lead sign to the signal of the local coil 50 by the receiver 70, may reduce or completely suppress the interference signal in the received signal of the local coil. However, for this, the actual interference signal is to be known as accurately as possible. Then, it is possible (e.g., by autocorrelation) to determine the proportion of the interference signal in the received signal of the local coil 50 and, by a suitable selection of phase shift and amplification or attenuation, to reduce the proportion of the interference signal significantly or eliminate the proportion of the interference signal entirely.

Therefore, according to the present embodiments, a sensor 60 is provided on the interference line in order to acquire the interference signal captured by the interference line and introduced into the patient tunnel 16 in an as unadulterated form as possible. Different embodiments of the sensor are described below.

Figure 2:
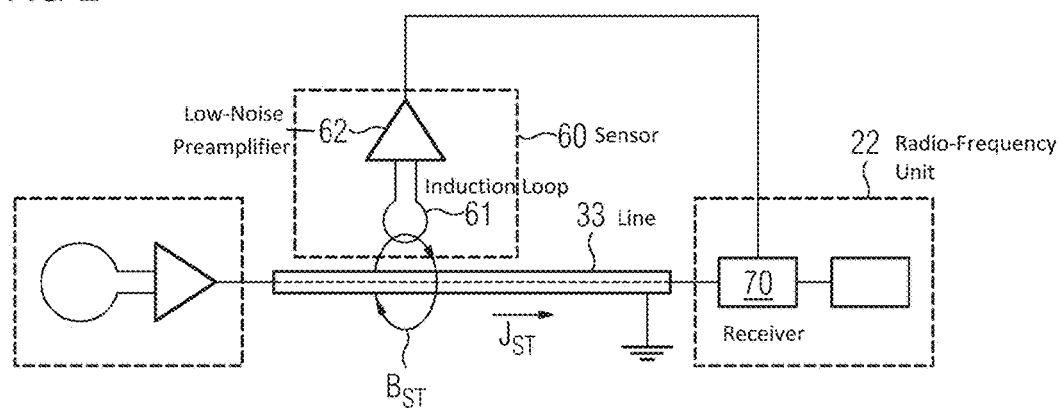
FIG. 2 is a schematic depiction of an embodiment of the line with a sensor.

FIG. 2 depicts by way of example the line 33 between the local coil 50 and the receiver 70 as an interference conductor. An alternating current $I_{ST}$ induced by an electromagnetic interference field flows on the outer conductor of the coaxial line. The source may be devices in other rooms or buildings. The alternating current $I_{ST}$ generates a magnetic alternating field $B_{ST}$ that surrounds the signal line 33 or the interference conductor. The sensor 60 according to the present embodiments uses this in that a coil or induction loop 61 is coupled to the magnetic interference field $B_{ST}$. The induction loop 61 may be aligned relative to the interference conductor such that a normal vector of an area enclosed by the induction loop 61 is oriented tangentially on the magnetic field lines of the magnetic field $B_{ST}$ extending in a circle about the signal line. In this way, the voltage induced in the induction loop 61 is at a maximum, and the sensor 60 delivers an interference signal that is as large and interference-free as possible. In one embodiment, the sensor 60 also includes a low-noise preamplifier 62 (LNA) that amplifies the induced signal before the induced signal is relayed via a sensor line 63 to the receiver 70. Herein, the induction loop 61 may also include a plurality of windings in order to increase the induced voltage. Herein, the induction loop 61 is galvanically isolated from the interference conductor.

In principle, instead of the coil or induction loop, other sensors 60 that are able to acquire a radio-frequency magnetic alternating field in amplitude and/or phase, such as, for example, Hall detectors, Josephson contacts, or a superconducting quantum interference device (SQID) may be provided.

Figure 3:
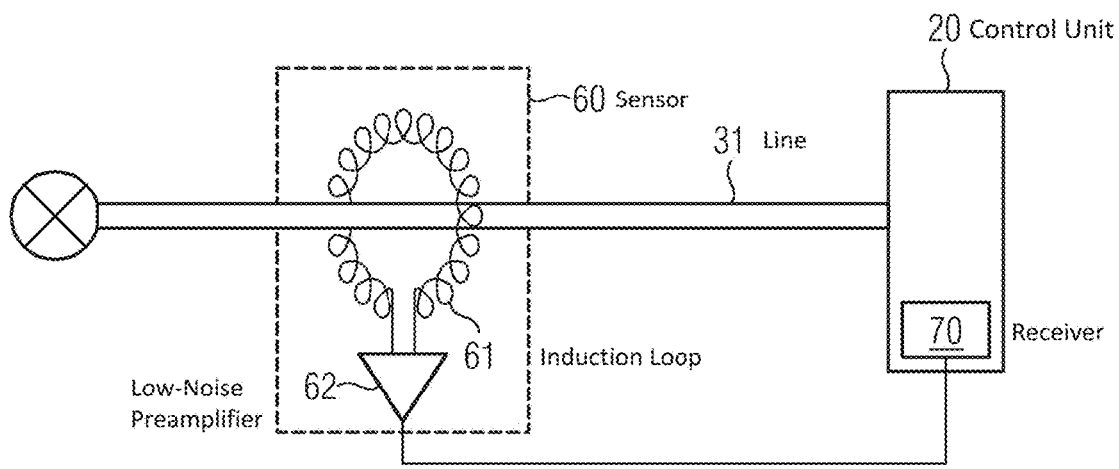
FIG. 3 is a schematic depiction of an embodiment of the line with a sensor.

FIG. 3 shows another embodiment of the sensor 60. By way of example, the sensor 60 is arranged on a line 31 for supplying energy to lighting (e.g., for the patient tunnel 16).

The sensor 60 may include an induction loop 61 with windings wound about a former enclosing the outer circumference of the line 33 or the interference conductor. In one embodiment, the actual former may be virtual (e.g., for the winding to be arranged in a self-supporting manner in this shape without a winding former.) In one embodiment, the former has the shape of a toroid or a cylindrical ring, but in another embodiment, instead of the ring, an ellipse, an ovoid, or a polygon, for example, encloses the interference conductor. In one embodiment, the cross section of the former and hence the shape of an individual winding of the induction loop 61 may have not only a circular shape, but, for example, also an elliptical shape, polygon, or even mixed shapes, such as a D shape. In other words, the individual windings extend around the former and are lined up around the circumference of the interference conductor so that, as depicted, two connectors of the induction loop 61 come to lie next to one another so that the two connectors may be returned to the low-noise preamplifier 62 with a small spacing and a small enclosed area.

Due to the extension along the field lines with a maximum area punctured by the field lines $B_{ST}$, an induction loop 61 shaped in this way has a maximum induced voltage. At the same time, the sensor is easy to push on and is insensitive to changes in position and external interference signals (e.g., interference signals that are not carried on the interference conductor).

Figure 4:
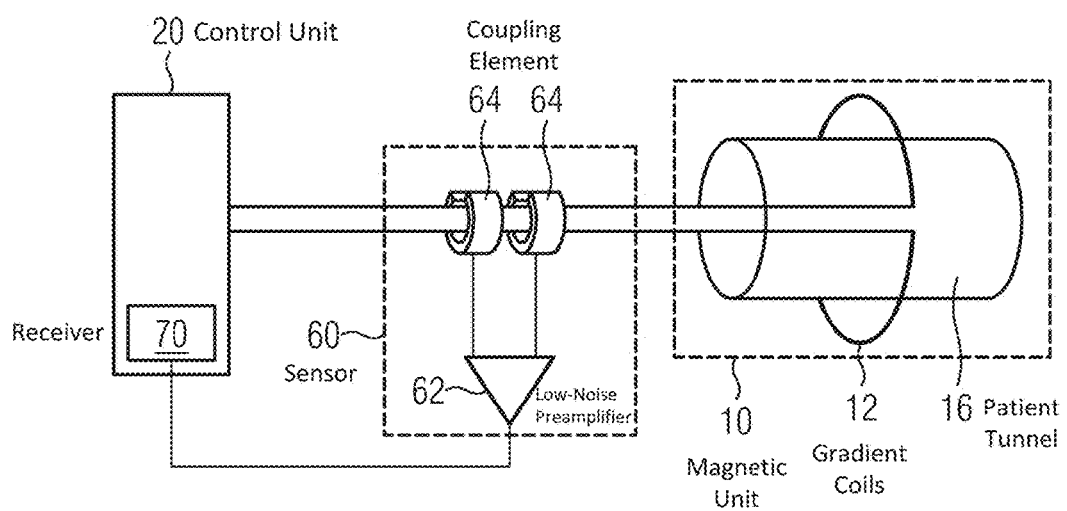
FIG. 4 is a schematic depiction of an embodiment of the line with a sensor.

FIG. 4 shows a further variant. Here, by way of example, a gradient connector line is assumed to be an interference line connecting the control system 20 to the gradient coils 12.

The interference signal is, for example, not picked up by induction, but capacitively via the electrical field component of the interference signal. In one possible embodiment, the sensor 60 may include one or, as depicted in FIG. 4, two capacitive coupling elements 64. These are arranged in the immediate vicinity (e.g., on the outside on an insulator) of the interference conductor and galvanically isolated therefrom. In one embodiment, the electrical field component of radio-frequency interference propagated along the interference conductor gives rise to voltage difference, which is amplified by the low-noise preamplifier 62 and fed to the receiver 70. In one embodiment, only one capacitive coupling element 64 may be provided, and the reference potential may be a signal ground.

Figure 5:
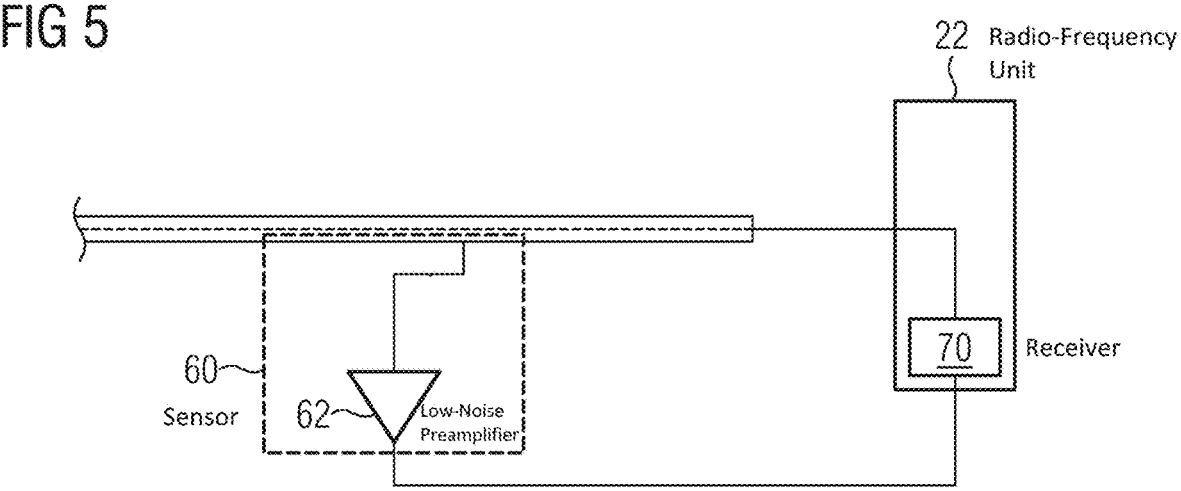
FIG. 5 is a schematic depiction of an embodiment of the line with a sensor.

The variant of the sensor depicted in FIG. 5 includes a directional coupler. In this context, a directional coupler is considered to be any type of signal pickup from the interference conductor that delivers a signal that is dependent on the propagation direction of the interference signal on the interference conductor. This may be a conventional directional coupler, but combinations of a plurality of inductive or capacitive coupling elements that deliver a direction-dependent signal may also be provided.

The directional coupler enables a differentiation to be made between signals with a propagation direction directed away from the local coil 50 and signals that are introduced into the local coil. Thus, a parasitic magnetic resonance signal on an outer conductor of the coaxial cable may be differentiated from an introduced interference signal so that the magnetic resonance signal is not erroneously identified as an interference signal resulting in the occurrence of artifacts caused by interference suppression during image evaluation.

Figure 6:
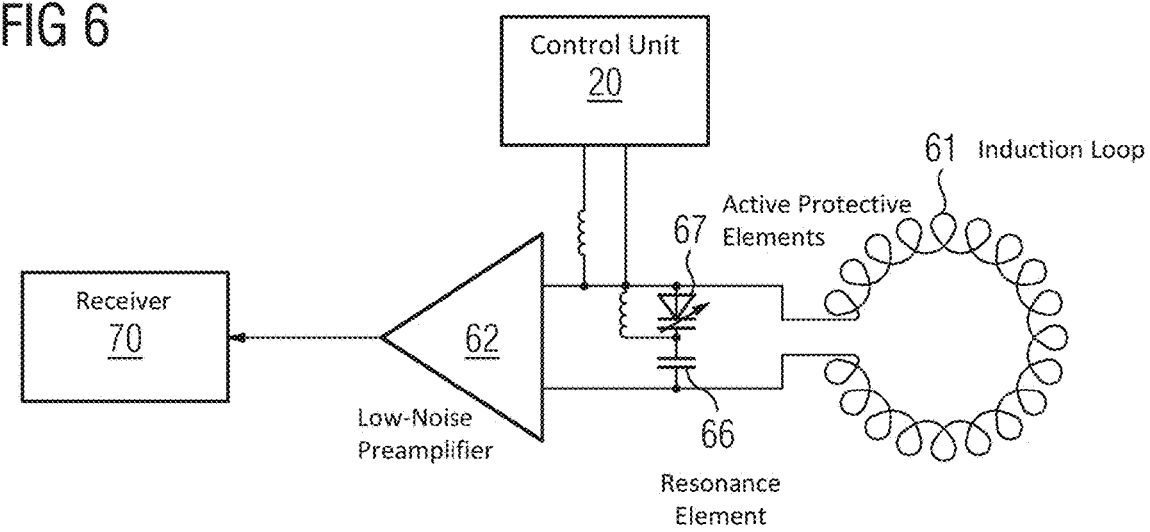
FIG. 6 is a schematic depiction of a sensor of an embodiment of the line.

In the embodiment in FIG. 6, the sensor 60 according to the present embodiments includes a resonance element 66 in order to render the sensor 60 particularly sensitive to a predetermined frequency (e.g., the Larmor frequency of the magnetic resonance tomography apparatus 1). Since the image acquisition takes place using magnetic resonance signals from nuclear spins, the frequency of which in the static magnetic field B0 corresponds to the Larmor frequency of the spins in this magnetic field, the image acquisition reacts particularly sensitively to interference in this frequency range. Therefore, better interference suppression is particularly effective and may be achieved by higher output signals from the sensor 60 in this frequency range. This may, for example, be achieved by a sensor resonance with a maximum amplitude at the Larmor frequency. For the toroidal coil depicted in FIG. 6 by way of example, this is possible by a capacitance as a resonance element 66 in an anti-resonant circuit.

A high dynamic range between the interference signal and the magnetic resonance signal, and the radio-frequency pulse for exciting the nuclear spins lead to the possibility (e.g., with a resonant sensor) that, for example, high input amplitudes during the excitation pulse will damage the sensor (e.g., the low-noise amplifier 62). Therefore, an active protective element 67 may be provided as protection (e.g., in the form of a pin diode), which, controlled by the control system 20, reduces the input signal of the low-noise amplifier 62. This may be achieved, as depicted in FIG. 6, in that, as a variable capacitance, the PIN diode detunes the resonant circuit consisting of the induction loop 61 and the resonance element 66. However, it may also be provided, for example, that the PIN diode may be operated as a switch that short-circuits the resonant circuit or detunes the resonant circuit using connected capacitances or inductances. In one embodiment, other mechanical or electronic switches may be used for this purpose.

FIG. 7 shows a further embodiment of the sensor 60 with a capacitive coupling element 64 that is tuned to the Larmor frequency by an inductance as a resonance element 66. FIG. 7 also includes the implementation of an exemplary passive protective element 68 consisting of two antiparallel diodes that short-circuit, and thus limit, any signal higher than the threshold voltage.

Other combinations of an inductive pick-up or induction loop 61 or capacitive coupling element 64 in each case with active protective elements 67 and/or passive protective elements 68 may also be provided within the sense of the present embodiments.

Although the invention was illustrated and described in greater detail by the exemplary embodiments, the invention is not restricted by the disclosed examples, and other variations may be derived herefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A line for an electrical connection in a magnetic resonance tomography apparatus with a connector to the magnetic resonance tomography apparatus, the line comprising:
   a conductor configured to pick up an electromagnetic interference signal from an environment, irradiate the electromagnetic interference signal into the environment, or a combination thereof;
   a sensor that is electrically, magnetically, or electrically and magnetically coupled to the conductor; and
   a signal connection configured to provide the electromagnetic interference signal picked up by the sensor at the connector to the magnetic resonance tomography apparatus for processing.

2. The line of claim 1, wherein the sensor comprises a coil configured for inductive coupling to the conductor.

3. The line of claim 2, wherein the conductor passes through an area enclosed by the coil.

4. The line of claim 3, wherein the coil is a toroidal coil that encloses the conductor.

5. The line of claim 1, wherein the sensor comprises a capacitive coupling element configured for coupling to the conductor.

6. The line of claim 1, wherein the sensor comprises a directional coupler.

7. The line of claim 1, wherein the sensor resonates at a Larmor frequency of the magnetic resonance tomography apparatus.

8. The line of claim 1, wherein the sensor is protected against an excitation pulse of the magnetic resonance tomography apparatus.

9. A magnetic resonance tomography apparatus comprising:
- a line for an electrical connection in the magnetic resonance tomography apparatus with a connector to the magnetic resonance tomography apparatus, the line comprising:
  - a conductor configured to pick up an electromagnetic interference signal from an environment, irradiate the electromagnetic interference signal into the environment, or a combination thereof;
  - a sensor that is electrically, magnetically, or electrically and magnetically coupled to the conductor; and
  - a signal connection configured to provide the electromagnetic interference signal picked up by the sensor at the connector to the magnetic resonance tomography apparatus for processing; and
- a control system configured to generate magnetic resonance imaging from received magnetic resonance signals in dependence on the electrical interference signal picked up by the sensor.

10. The magnetic resonance tomography apparatus of claim 9, wherein the sensor is arranged adjacent to a patient tunnel.

11. The magnetic resonance tomography apparatus of claim 9, wherein the sensor comprises a coil configured for inductive coupling to the conductor.

12. The magnetic resonance tomography apparatus of claim 11, wherein the conductor passes through an area enclosed by the coil.

13. The magnetic resonance tomography apparatus of claim 12, wherein the coil is a toroidal coil that encloses the conductor.

14. The magnetic resonance tomography apparatus of claim 9, wherein the sensor comprises a capacitive coupling element configured for coupling to the conductor.

15. The magnetic resonance tomography apparatus of claim 9, wherein the sensor comprises a directional coupler.

16. The magnetic resonance tomography apparatus of claim 9, wherein the sensor resonates at a Larmor frequency of the magnetic resonance tomography apparatus.

17. The magnetic resonance tomography apparatus of claim 9, wherein the sensor is protected against an excitation pulse of the magnetic resonance tomography apparatus.

* * * * *